(12) United States Patent
Minami et al.

(10) Patent No.: US 6,197,343 B1
(45) Date of Patent: Mar. 6, 2001

(54) SKIN COLOR IMPROVER

(75) Inventors: Takahide Minami; Akiko Suzuki; Hidetaka Iwai; Yukihiro Yada; Yoshinao Nagashima, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/147,077

(22) PCT Filed: Mar. 28, 1997

(86) PCT No.: PCT/JP97/01085

§ 371 Date: Oct. 1, 1998

§ 102(e) Date: Oct. 1, 1998

(87) PCT Pub. No.: WO97/36571

PCT Pub. Date: Oct. 9, 1997

(30) Foreign Application Priority Data

Apr. 1, 1996 (JP) .................................................. 8-078682

(51) Int. Cl.⁷ ....................................................... A61K 9/14
(52) U.S. Cl. ............................................ 424/489; 424/401
(58) Field of Search ................................... 424/489, 401, 424/78.02, 465, 464

(56) References Cited

U.S. PATENT DOCUMENTS

| 4,724,240 | 2/1988 | Abrutyn . |
| 4,855,127 | 8/1989 | Abrutyn et al. . |
| 4,880,617 | 11/1989 | Chromecek et al. . |
| 5,538,728 | * 7/1996 | Yanaki et al. ................. 424/401 |

FOREIGN PATENT DOCUMENTS

| 0 376 852 | 7/1990 | (EP) . |
| 61-207312 | 9/1986 | (JP) . |
| 6-321737 | 11/1994 | (JP) . |
| WO 95/19376 | 7/1995 | (WO) . |

* cited by examiner

Primary Examiner—Thurman K. Page
Assistant Examiner—William E. Benston, Jr.
(74) Attorney, Agent, or Firm—Oblon, Spivak, McClelland, Maier & Neustadt, P.C.

(57) ABSTRACT

The invention relates to a complexion-improving beauty composition comprising disintegrable granules and a blood circulation accelerator. The composition can synergistically exhibit a blood circulation-accelerating effect in a short period of time, is excellent in the effect of improving a complexion, and does not irritate the skin and eyes, thus being highly safe.

12 Claims, No Drawings

SKIN COLOR IMPROVER

This appln is a 371 of PCT/JP97/01085 filed Mar. 28, 1997.

TECHNICAL FIELD

The present invention relates to complexion-improving beauty compositions, and more particularly to complexion-improving beauty compositions which cause high penetration of a component for positively improving peripheral circulation, are excellent in the effect of preventing and improving the uneven tone, dull looking and lusterlessness of skin, which are caused by the irregularity of blood circulation, and do not irritate the skin and eyes, thus being highly safe.

BACKGROUND ART

Investigations as to various cosmetic compositions for accelerating the blood circulation of the skin have heretofore been made with the view toward preventing and improving the uneven tone, dull looking and lusterlessness of skin, which are caused by the irregularity of blood circulation. For example, cosmetic compositions in which a blood circulation accelerator is incorporated (Japanese Patent Application Laid-Open Nos. 138411/1987 and 321616/1992, etc.), and techniques in which the content of water is decreased to the utmost, and a polyol is incorporated at a high concentration so as to generate heat upon application and raise the temperature of the skin applied, thereby accelerating the circulation of the blood (Japanese Patent Application Laid-Open Nos. 229926/1993, 320038/1993 and 9280/1994), and the like have been known.

However, the cosmetic compositions simply comprising the blood circulation accelerator have required a high concentration of the blood circulation accelerator or a long time in order that the effect of the blood circulation accelerator may be recognized, and may have given users an irritated feeling toward the skin in cases where such an agent has been incorporated at a high concentration. On the other hand, the cosmetic compositions of the type that the temperature of the skin is raised have had an abnormal feel of stickiness or sliminess and besides have involved a problem that they tend to give users a feeling of glow, since the polyol has been incorporated in a large amount.

Also having been investigated are massaging cosmetic compositions (Japanese Patent Application Laid-Open Nos. 44649/1976, 183205/1986, 211206/1988, 90011/1991 and 157279/1994) used for accelerating the blood circulation by applying physical stimulation, and massaging cosmetic compositions (Japanese Patent Application Laid-Open No. 44649/1976, Japanese Patent Publication No. 42203/1985, and Japanese Patent Application Laid-Open Nos. 192814/1983 and 295504/1988) to which particles are added for enhancing physical stimulation. However, the massaging cosmetic compositions to which the particles are added have involved a problem that the effect of the particles are scarcely brought about when their particle size is smaller than 100 µm, or on the other hand when the particle size is not smaller than 100 µm, they give users a feeling of physical disorder during use, and damage the skin if time used or the frequency of use becomes high.

Further, techniques for enhancing safety by using granules, which are gradually disintegrated by inunction (rubbing) or massaging, have come to be investigated (Japanese Patent Publication Nos. 39444/1992 and 53649/1994, and Japanese Patent Application Laid-Open Nos. 190616/1989, 197412/1991, 221826/1993 and 271417/1994). Even when such granules have been used, the resulting cosmetic compositions have brought about no sufficient effects for accelerating the circulation of the blood and improving a complexion.

Accordingly, it is an object of the present invention to provide a complexion-improving beauty composition which is excellent in the effect of improving a complexion and has high safety.

DISCLOSURE OF THE INVENTION

In view of the foregoing circumstances, the present inventors have carried out an extensive investigation. As a result, it has been found that beauty compositions comprising disintegrable granules and a blood circulation accelerator can synergistically exhibit a blood circulation-accelerating effect in a short period of time, do not irritate the skin and eyes and can markedly improve a complexion, thus leading to completion of the present invention.

According to the present invention, there is thus provided a complexion-improving beauty composition comprising disintegrable granules and a blood circulation accelerator.

According to the present invention, there is also provided a method of improving a complexion, which comprises applying a composition comprising disintegrable granules and a blood circulation accelerator to the skin and then massaging or rubbing the skin applied.

BEST MODE FOR CARRYING OUT THE INVENTION

The disintegrable granules useful in the practice of the present invention are those having strength that they are easily disintegrated on the skin when applied to the skin. In order that the granules may be easily disintegrated, they preferably have a strength of 2 to 8 as measured by a Vickers hardness test (JIS Z 2244) and a strength of 0.05 to 0.80 kgf/mm$^2$, particularly 0.08 to 0.30 kgf/mm$^2$ as measured by a flexural test (JIS R 1601), both making use of a specimen made so as to have the same composition as the granules.

Examples of such disintegrable granules include granules composed of water-insoluble primary particles and a binder.

Examples of the water-insoluble primary particles include organic polymer compounds such as polyethylene, polystyrene, polyester, polyvinyl chloride, polyamide, polypropylene, nylon, polyvinylidene fluoride, polyurethane, acrylic resins, polysiloxane, crystalline cellulose, starch and derivatives thereof; and inorganic powders such as silica, alumina, talc, kaolin, titanium oxide, zinc oxide, quartz and calcium phosphate. These primary particles may be in any form of a spherical or an amorphous form. However, the spherical form is particularly preferred from the viewpoint of safety. The average particle size of the primary particles is preferably 1 to 20 µm, particularly 3 to 15 µm. Taking the safety of eyes into consideration, it is preferred that at least 80 wt. % of the primary particles should have a particle size of 10 µm or smaller, particularly 4 to 10 µm.

The binder is used for binding the water-insoluble primary particles to one another to such strength that the resulting disintegrable granules are easily disintegrated on the skin. Examples thereof include animal and vegetable oils which are solid at ordinary temperature, such as fish oil, hardened castor oil and hardened rapeseed oil; and organic polymer compounds such as ethyl cellulose, acetyl cellulose, nitrocellulose, hydroxymethyl cellulose, hydroxyethyl cellulose, hydroxypropyl cellulose, polyvinyl pyrrolidone and vinyl acetate.

The disintegrable granules composed of these water-insoluble primary particles and binder can be prepared by a general granulating process, for example, fluidized bed granulation, agitation granulation or extrusion granulation. In particular, they may preferably be prepared in accordance with a process in which a water-insoluble binder is dissolved in an organic solvent, and the solvent is volatilized, thereby preparing granules (Japanese Patent Application Laid-Open No. 152407/1985), or a process in which powder of a water-insoluble binder is mixed with primary particles of granules, the mixture is granulated with a water-soluble binder, and the resultant granules are heated to melt the powder of the water-insoluble binder, and then cooled, thereby enhancing the water resistance of the granules (Japanese Patent Application Laid-Open No. 271417/1994). The disclosures of Japanese Patent Application Laid-Open Nos. 152407/1985 and 271417/1994 are incorporated herein by reference.

Of such disintegrable granules, disintegrable granules obtained by using polyethylene as the primary particles, and hydroxypropyl cellulose, hardened rapeseed oil and/or the like as the binder are preferred.

The particle size of the disintegrable granules is preferably 100 to 1,000 µm, particularly 200 to 600 µm. When the particle size falls within this range, the resulting beauty composition has a sufficient effect for improving a complexion and gives users no too strong stimulative feeling.

These disintegrable granules may be used either singly or in any combination thereof and are preferably incorporated in a proportion of 0.1 to 5 wt. % (hereinafter indicated merely by "%"), more preferably 0.5 to 3%, most preferably 0.8 to 2% based on the total weight of the composition, since the beauty composition provided has a sufficient effect for improving a complexion and gives no feeling of physical disorder upon use.

Any agent may be used as the blood circulation accelerator used in the present invention so far as it is an ingredient commonly used in the classical cosmetic compositions, quasi-drugs and drugs. Compounds, plant extracts and the like may be used without any particular limitation.

Specifically, examples of the compounds include the esterified products, nicotinate and orotate of vitamin E, which are described as vasodilators in Japanese Patent Application Laid-Open No. 87506/1987; the esterified products, acetate and succinate of vitamin E, which are described as periphery circulation accelerators in Japanese Patent Application Laid-Open No. 195316/1987; and besides nicotinic acid amide, methyl nicotinate and the like. Examples of the plant extracts include extracts which are clearly described as having a blood circulation-accelerating effect in Fragrance Journal, Extra Edition Vol. 6, issued in 1986 and Fragrance Journal, Extra Edition Vol. 1, issued in 1979, for example, extracts from arnica, Japanese hawthorn, quinine tree, scarlet sage, *Tilia europaea* L, *Panax ginseng* C. A. Meyer, juniper, rosemary, Saint-John's-wort, ginkgo, melissa, petty white-root, *marronnier*, Japanese green gentian, garlic, chamomile, cyme, Japanese mint, nettle, red pepper, ginger, hop, horse chestnut, lavender, carrot, brown mustard, cinnamon, pine, *Cnidium ooficinale* Makino, elder, Japanese parsley, *Scopolia japonicus* Hara, peony, myrica, *Houttuynia cordata*, candock, astringent persimmon, pot marigold, field poppy, gentian, grapes, *Glehnia littoralis*, bitter orange, citron, calamus, Watson pomelo, hamamelis, melilot, fennel, Japanese pepper tree, peony, eucalyptus, mugwort, *Isodon japonicus* Hara, rice, *Sophora flavescence* Aiton, ginger and clove. The disclosures of Japanese Patent Application Laid-Open Nos. 87506/1987 and 195316/1987, Fragrance Journal, Extra Edition Vol. 6, and Fragrance Journal, Extra Edition Vol. 1 are incorporated herein by reference.

Of these, tocopherol nicotinate, nicotinic acid amide are preferred as the compounds, while Japanese green gentian extract, Saint-Jone's-wort extract, ginkgo extract, arnica extract, hamamelis extract, pot marigold extract, *marronnier* extract, *Isodon japonicus* Hara extract, scarlet sage extract, *Glehnia littoralis* extract, rice germ oil and *Tilia europaea* L extract are preferred as the plant extracts.

Tocopherol nicotinate, *Tilia europaea* L extract and *marronnier* extract are particularly preferred.

These blood circulation accelerators may be used either singly or in any combination thereof and are preferably incorporated in a proportion of 0.001 to 5% based on the total weight of the composition. In particular, it is preferred that they are incorporated in a proportion of 0.01 to 3%, further 0.02 to 2%, since a beauty composition having a sufficient effect for improving a complexion and giving no feeling of glow can be provided. Incidentally, in the case of the plant extracts, it is preferred that the incorporated amount in terms of dry solids should fall within the above range.

In the complexion-improving beauty compositions according to the present invention, at least one ingredient selected from an oily substance, whitening agent and sebum secretion inhibitor may be further incorporated. By incorporating such ingredients, the complexion-improving effect can be more enhanced.

Of these, the oily substance is such that can prevent irregular reflection of light, impart good luster to the skin and smooth the irregularity of a complexion. In order to more enhance the complexion-improving effect, the oily substance preferably has a refractive index of at least 1.444 or an SP value of at least 16.5. The term "SP value" as used herein means a solubility parameter calculated from organicity and inorganicity.

Specifically, examples of oily substances having a refractive index of at least 1.444 include isotridecyl isononanoate, glyceryl tri-2-ethylhexanoate, neopentyl glycol dicaprate, 1-isostearoyl-3-myristoylglycerol, diisostearyl adipate, liquid isoparaffin, squalane, diglyceryl monoisostearate, diglyceryl diisostearate, diglyceryl triisostearate, glyceryl tri (caprylate caprate), isotridecyl myristate, octyldodecyl myristate, hexyldecyl myristate, octyldodecyl neodecanoate, evening primrose oil, jojoba oil, abocado oil, grape oil, turtle oil, mink oil, orange raffinate oil and polyoxyethylenemethyl polysiloxane copolymers. Examples of oily substances having an SP value of at least 16.5 include isotridecyl isononanoate, diglyceryl triisostearate, diglyceryl tetraisostearate, trimethylolpropane triisostearate, neopentyl glycol dioctanoate, diisostearyl malate, octyldodecyl lactate, glyceryl tri-2-ethylhexanoate, 1-isostearoyl-3-myristoylglycerol 1,3-myristoylglycerol and isostearyl adipate.

Of these, isotridecyl isononanoate, neopentyl glycol dicaprate, 1-isostearoyl-3-myristoylglycerol, glyceryl tri-2-ethylhexanoate, squalane, 1,3-myristoylglycerol, diglyceryl monoisostearate, diglyceryl diisostearate, diglyceryl triisostearate and octyldodecyl lactate are preferred, with isotridecyl isononanoate, neopentyl glycol dicaprate and 1-isostearoyl-3-myristoylglycerol being particularly preferred.

These oily substances may be used either singly or in any combination thereof and are preferably incorporated in a proportion of 1 to 20%, particularly 3 to 17% based on the total weight of the composition.

The whitening agent is such that can improve spots, freckles and a dark complexion caused by a melanin pigment. For example, such agents may be used as ascorbic acid and derivatives thereof, hydroquinone derivatives, kojic acid and derivatives thereof, placenta extracts, plant extracts, and the like, which are disclosed in "Fragrance Journal, Extra Edition Vol. 14 (1995)" and are in common use as whitening agents. The disclosure of Fragrance Journal, Extra Edition Vol. 14 is incorporated herein by reference.

Specifically, examples of ascorbic acid and derivatives thereof include alkali metal salts of L-ascorbic acid phosphate such as sodium L-ascorbic acid phosphate and potassium L-ascorbic acid phosphate; alkaline earth metal salts of L-ascorbic acid phosphate such as magnesium L-ascorbic acid phosphate and calcium L-ascorbic acid phosphate; trivalent metal salts of L-ascorbic acid phosphate such as aluminum L-ascorbic acid phosphate; alkali metal salts of L-ascorbic acid sulfate such as sodium L-ascorbic acid sulfate and potassium L-ascorbic acid sulfate; alkaline earth metal salts of L-ascorbic acid sulfate such as magnesium L-ascorbic acid sulfate and calcium L-ascorbic acid sulfate; trivalent metal salts of L-ascorbic acid sulfate such as aluminum L-ascorbic acid sulfate; alkali metal salts of L-ascorbic acid such as sodium L-ascorbate and potassium L-ascorbate; alkaline earth metal salts of L-ascorbic acid such as magnesium L-ascorbate and calcium L-ascorbate; and trivalent metal salts of L-ascorbic acid such as aluminum L-ascorbate.

Examples of the hydroquinone derivatives include condensates of hydroquinone with a saccharide, and condensates of an alkylhydroquinone obtained by introducing an alkyl group having 1 to 4 carbon atoms into hydroquinone with a saccharide.

Examples of kojic acid and derivatives thereof include kojic acid, monoesters such as kojic acid monobutyrate, kojic acid monocaprate, kojic acid monopalmitate, kojic acid monostearate, kojic acid monocinnamate and kojic acid monobenzoate, and diesters such as kojic acid dibutyrate, kojic acid dipalmitate, kojic acid distearate and kojic acid dioleate.

As the placenta extract, may be used those generally marketed as water-soluble placenta extracts and used as cosmetic raw materials. Examples thereof include those obtained by subjecting a placenta of a mammal such as bovine, swine or human to washing, depletion of blood, shredding, freezing and the like to extract a water-soluble component and then removing impurities from the water-soluble component.

Examples of the plant extracts include extracts from licorice, puerariae root, soybean, trillum, *Tulipa edulis*, *Anemarrhena asphodeloides* Bunge, *Ophiopogon japonicus* Ker-Gawler, sansevieria, white oak, *Artemisia capillaris* Thunb, chamomile, artichoke, aster, rice, clove, turmeric, balsam pear, *Dioscoreae rhizoma*, aloe, tea plant, creeping saxifrage, *Scutellaria baicalensis* Georgi, loquat, orange peal, ginseng, althea, quinine tree, common comfrey, rosemary, scopolia rhizome and gulfweed.

Of these, L-ascorbic acid, arbutin, kojic acid, placenta extracts, chamomile extract, tea plant extract, puerariae root extract and licorice extract are particularly preferred.

These beautifying agents may be used either singly or in any combination thereof and are preferably incorporated in a proportion of 0.01 to 10%, particularly 0.1 to 5% (in terms of dry solids in the case of a plant extract) based on the total weight of the composition.

The sebum secretion inhibitor serves to prevent pigmentation and skin roughness around pores of the skin, acne and the like caused by hypersteatosis. For example, such agents may be used as anti-androgenic agents, crude drug extracts, astringents and the like, which are disclosed in "Fragrance Journal, Vol. 10 (1994)" and are in common use as sebum secretion inhibitors. The disclosure of Fragrance Journal, Vol. 10 (1994) is incorporated herein by reference.

Specifically, examples of the anti-androgenic agents include oxendolone, 17-α-methyl-β-nortestosterone, chlormadinone acetate, cyproterone acetate, spironolactone, hydroxyflutamide, estradiol and ethinyl estradiol.

Examples of the crude drug extracts include extracts from leaves of walnut, *Scutellaria baicalensis* Georgi, sage, hop, rosemary, Saint-Jone's-wort, Japanese mint, chamomile, cashew, goldthread, Amur cork tree, OREI, *Houttuyniae herba*, dried orange peal, carrot, peony, mat rush, propolis, *Alismatis rhizoma*, tannin, hamamelis, peony and birch tar, and royal jelly and yeast extract.

Examples of the astringents include zinc sulfocarbolate, zinc oxide, aluminum hydroxychloride and (allantoinato) dihydroxyaluminum.

Besides, vitamin $B_6$, 13-cis-retinoic acid, vitamin E, glycyrrhetinic acid, salicylic acid, nicotinic acid, calcium pantothenate, dipotassium azelate, 10-hydroxyundecanoic acid, 12-hydroxystearic acid and the like may also be used as sebum secretion inhibitors.

Of these, estradiol, zinc sulfocarbolate, zinc oxide, royal jelly, 10-hydroxyundecanoic acid and 12-hydroxystearic acid are particularly preferred.

These sebum secretion inhibitors may be used either singly or in any combination thereof and are preferably incorporated in a proportion of 0.01 to 10%, particularly 0.1 to 5% (in terms of dry solids in the case of a crude drug extract) based on the total weight of the composition.

In the complexion-improving beauty compositions according to the present invention, ingredients commonly used in the classical external skin care compositions, detergent compositions, cosmetic compositions and massaging compositions may be suitably incorporated in addition to the above-described components so far as no detrimental influence is thereby imposed on the effects of the present invention. They are, for example, moisturizers, softeners, surfactants, keratin protecting agents, thickeners, antiseptics, pH adjusters, perfume bases, antioxidants, colorants, medicinally-effective agents other than those mentioned above, and solvents.

No particular limitation is imposed on the moisturizers of these. However, examples thereof include ethylene glycol, diethylene glycol, triethylene glycol and still higher polyethylene glycols; propylene glycol, dipropylene glycol and still higher polypropylene glycols; butylene glycols such as 1,3-butylene glycol and 1,4-butylene glycol; glycerol, diglycerol and still higher polyglycerols; sugaralcohols such as sorbitol, mannitol, xylitol and maltitol; adducts of glycerols with ethylene oxide (hereinafter abbreviated as "EO") or propylene oxide (hereinafter abbreviated as "PO"); adducts of sugaralcohols with EO or PO; monosaccharides such as galactose and fructose, and EO or PO adducts thereof; polysaccharides such as maltose and lactose, and EO or PO adducts thereof; sodium pyrrolidonecarboxylate; and polyoxyethylene methylglucosides (number of moles of EO added: 10, 20, etc.).

No particular limitation is imposed on the softeners. However, examples thereof include α-hydroxy acids such as α-hydroxyisobutyric acid, α-hydroxyisocaproic acid, α-hydroxy-n-capronic acid, α-hydroxyisocaprylic acid, α-hydroxy-n-caprylic acid, α-hydroxy-n-capric acid, lactic acid, α-hydroxystearic acid, citric acid and glycolic acid; basic amino acids such as lysine, arginine, histidine, ornithine and canavanine; amines such as ε-aminocaproic acid, urea, 2-hydroxyguanidine and 2-(2-hydroxyethoxy) ethylguanidine; and beside peptides described in Japanese Patent Application Laid-Open Nos. 99315/1987 and 178207/1990, and trimethylglycine described in Japanese Patent Application Laid-Open No. 293625/1994. The disclosures of Japanese Patent Application Laid-Open Nos. 99315/1987, 178207/1990 and 293625/1994 are incorporated herein by reference.

As the surfactants, any surfactants of nonionic surfactants, anionic surfactants, cationic surfactants and amphoteric surfactants may be used without any particular limitation. However, examples thereof include polyoxyethylene (hereinafter abbreviated as "POE") hardened castor oil, POE alkyl ethers, POE branched alkyl ethers, POE fatty acid esters, POE glycerol fatty acid esters, POE sorbitan fatty acid esters, POE sorbitol fatty acid esters, POE hardened castor oil alkylsulfates, POE alkyl sulfates, polyglycerol fatty acid esters, alkyl phosphates, POE alkyl phosphates, alkali metal salts of fatty acids, sorbitan fatty acid esters, glycerol fatty acid esters, alkyl polyglucosides, polyethylene glycol fatty acid esters, α-monoisostearyl glyceryl ether, sodium stearoyl methyltaurine, sodium POE lauryl ether phosphate and ether-modified silicones.

No particular limitation is imposed on the keratin protecting agents. However, examples thereof include mucopolysaccharides such as hyaluronic acid and chondroitin sulfate, proteins such as gelatin and collagen, and acid hetero-polysaccharides described in Japanese Patent Application Laid-Open No. 10997/1989.

No particular limitation is imposed on the thickeners. However, examples thereof include high-molecular compounds such as carrageenan, dextrin, methyl cellulose, ethyl cellulose, hydroxyethyl cellulose, hydroxypropyl cellulose, polyvinyl alcohol, polyacrylic acid, sodium polyacrylate, polymethacrylic acid, carboxyvinyl polymers, xanthan gum, carboxymethylchitin, chitosan and cationized cellulose, and inorganic compounds such as aluminum magnesium silicate and bentonite.

The complexion-improving beauty compositions according to the present invention can be provided in various forms such as liquid, solid, paste, jelly, O/W emulsion and W/O emulsion. In particular, they may preferably be provided as O/W type emulsified compositions or water-based compositions. They may also be provided as compositions of such a type that they are only applied, that they are washed out after massaging, or that they are wiped out after massaging.

In the present invention, it goes without saying that upon incorporation of the disintegrable granules, such disintegrable granules should be chosen for use that are not disintegrated by a solvent, taking the content of a solvent like water or alcohol into consideration.

The complexion-improving beauty compositions according to the present invention may be used by applying them to a face, neck and/or the like by the conventional method. However, a higher effect can be brought about by massaging or rubbing with hands after application of the composition.

When the complexion-improving beauty composition is used with massaging or inunction, it may be enough to take a necessary amount, for example, 2 to 4 g, of the composition in user's hands, lightly apply it to a face, neck and/or the like, lightly massage the part applied with the palm of the hand or the inner surfaces of fingers until the disintegrable granules are disintegrated, namely the feel of the disintegrable granules disappears (for about 30 seconds), and wipe the composition out with a tissue or cotton or wash it out with water or hot water.

EXAMPLES

The present invention will hereinafter be described more specifically by the following Examples. However, the present invention is not limited to these examples.

Incidentally, the incorporated amounts of plant extracts used in the examples were all expressed in terms of dry solids.

Examples 1 to 18 and Comparative Examples 1 to 3

Water-based, complexion-improving beauty compositions in the form of jelly were prepared by stirring and mixing components of their corresponding formulations shown in Tables 1 and 2 in accordance with a method known per se in the art to evaluate them as to blood circulation-accelerating effect, complexion-improving effect, etc. The results are shown in Tables 1 and 2.

Evaluation Methods
(1) Blood Circulation-Accelerating Effect

Each (about 1 g) of the complexion-improving beauty compositions of Examples 1 to 18 and Comparative Examples 1 to 3 was rubbed with hands in the cheek of each of healthy persons (5 men and 6 women) aged 20 to 40 years. After the subject was given a 10-minute rest, a blood stream at the part applied was measured by means of a blood flowmeter (Laser Doppler blood flowmeter, manufactured by Biomedical Science Co.). The blood stream was also measured in the same manner as described above after a rest before the application of the complexion-improving beauty composition. Assuming that the respective blood streams are A and B, a percent increase of blood stream was determined in accordance with the following equation:

Percent increase (VS) of blood stream after the 10-minute rest:

$$VS=(A/B)\times 100(\%)$$

On the other hand, the cheek of each of the subjects was rubbed without applying the complexion-improving beauty composition to measure a blood stream at the part rubbed. Assuming that a percent increase of blood stream at that time is VB, a blood circulation-accelerating effect (V) was determined in accordance with the following formula:

$$V=VS-VB$$

The sample composition was evaluated as to the blood circulation-accelerating effect by giving a score 1 where V was greater than 0, or a score 0 where V was not greater than 0 to average the scores of the eleven subjects, and ranked as ○ where the average value was a score 1, or × where the average value was a score 0, when it was rounded at the first decimal place.

(2) Complexion-Improving Effect

Each (about 2 g) of the complexion-improving beauty compositions of Examples 1 to 23 and Comparative Examples 1 to 3 was applied to the cheek of each of healthy persons (5 men and 5 women) aged 20 to 40 years, and the part applied was rubbed with subject's own hands. This process was continuously conducted for 6 weeks once a day. After completion of the 6-week inunction test, the degree of complexion irregularity at the subject's cheeks was classified into the following 4 scores to average scores visually judged by 5 expert judges, thereby conducting a T-test assuming that the scores of complexion irregularity before and after the test were $S_0$ and $S_1$, respectively, to evaluate the sample composition as to the complexion-improving effect and rank it as ○ where $S_1$ showed a significant (P<0.01) low value compared with $S_0$, or × where no significant low value was shown.

Score of Complexion Irregularity

Score 1: No complexion irregularity was observed;
Score 2: Slight complexion irregularity was observed;
Score 3: Moderate complexion irregularity was observed;
Score 4: Severe complexion irregularity was observed.

(3) Organoleptic Evaluation

After the test on the complexion-improving effect, the subjects were got to organoleptically evaluate the sample compositions as to a complexion-improving effect and a feeling of irritation or physical disorder toward the skin and eyes.

Each of the sample compositions was ranked as ○ where at least four subjects of six judged that the composition was good, Δ where three subjects judged so, or × where at most two subjects judged so.

(4) Overall Evaluation

Each of the sample compositions was ranked as ○ where it was ranked as ○ as to all the evaluation items of blood circulation-accelerating effect, complexion-improving effect and organoleptic evaluation, or Δ as to one evaluation item and ○ as to the other evaluation items, or × where it was ranked as Δ as to two evaluation items, or × even as to one evaluation item.

TABLE 1

| Component incorporated (%) | Example 1 | 2 | 3 | 4 | 5 | 6 | 7 | 8 | 9 | 10 | 11 | 12 |
|---|---|---|---|---|---|---|---|---|---|---|---|---|
| 1) Purified water | 89.9 | 89.4 | 93.4 | 86.5 | 92.8 | 91.9 | 91.9 | 91.9 | 91.9 | 91.9 | 91.9 | 91.9 |
| 2) Disintegrable granules 1[*1] | 1 | 0.5 | 0.5 | 2 | 0.5 | 1 | 1 | 1 | 1 | 1 | 1 | 1 |
| 3) Disintegrable granules 2[*2] | | 0.5 | | 1 | | | | | | | | |
| 4) Polyethylene powder[*3] | | | | | | | | | | | | |
| 5) dl-α-Tocopherol nicotinate | 1 | 0.5 | 0.5 | 0.5 | 0.5 | | | | | | | |
| 6) Nicotinic acid amide | | | | | | 1 | | | | | | |
| 7) Japanese green gentian extract | | | | | 0.5 | | 1 | | | | | |
| 8) Saint-Jone's-wort extract | | | | | | | | 1 | | | | |
| 9) Ginkgo extract | | | | | | | | | 1 | | | |
| 10) Arnica extract | | | | | | | | | | 1 | | |
| 11) Hamamelis extract | | | | | | | | | | | 1 | |
| 12) Pot marigold extract | | | | | | | | | | | | 1 |
| 13) Marronnier extract | | | | | | | | | | | | |
| 14) *Isodon japonicus* Hara extract | | | | | | | | | | | | |
| 15) Scarlet sage extract | | | | | | | | | | | | |
| 16) *Glehnia littoralis* extract | | | | | | | | | | | | |
| 17) Rice germ oil | | | | | | | | | | | | |
| 18) *Tilia europaea* L extract | | | | | | | | | | | | |
| 19) Polyoxyethylene hardened castor oil | 1 | 1 | 0.8 | 0.8 | 0.8 | 1 | 1 | 1 | 1 | 1 | 1 | 1 |
| 20) Carboxyvinyl polymer | 0.5 | 0.5 | 0.4 | 0.55 | 0.5 | 0.5 | 0.5 | 0.5 | 0.5 | 0.5 | 0.5 | 0.5 |
| 21) 3% Water-soluble collagen solution | 1 | 2 | 1 | 3 | 1 | 3 | 3 | 3 | 3 | 3 | 3 | 3 |
| 22) Glycerol | 5 | 5 | 3 | 5 | 3 | 1 | 1 | 1 | 1 | 1 | 1 | 1 |
| 23) L-Arginine | 0.5 | 0.5 | 0.3 | 0.5 | 0.3 | 0.5 | 0.5 | 0.5 | 0.5 | 0.5 | 0.5 | 0.5 |
| 24) Perfume base | 0.01 | 0.01 | 0.01 | 0.01 | 0.01 | 0.01 | 0.01 | 0.01 | 0.01 | 0.01 | 0.01 | 0.01 |
| 25) Methyl p-hydroxybenzoate | 0.1 | 0.1 | 0.05 | 0.1 | 0.05 | 0.05 | 0.05 | 0.05 | 0.05 | 0.05 | 0.05 | 0.05 |
| Blood circulation-accelerating effect | ○ | ○ | ○ | ○ | ○ | ○ | ○ | ○ | ○ | ○ | ○ | ○ |
| Complexion-improving effect | ○ | ○ | ○ | ○ | ○ | ○ | ○ | ○ | ○ | ○ | ○ | ○ |
| Organoleptic evaluation (complexion improvement) | ○ | ○ | Δ | ○ | ○ | ○ | ○ | ○ | ○ | ○ | ○ | ○ |
| Organoleptic evaluation (feeling of irritation or physical disorder) | ○ | ○ | ○ | ○ | ○ | ○ | ○ | ○ | ○ | ○ | ○ | ○ |
| Overall evaluation | ○ | ○ | ○ | ○ | ○ | ○ | ○ | ○ | ○ | ○ | ○ | ○ |

TABLE 2

| Component incorporated (%) | Example 13 | 14 | 15 | 16 | 17 | 18 | Comp. Example 1 | 2 | 3 |
|---|---|---|---|---|---|---|---|---|---|
| 1) Purified water | 91.9 | 91.9 | 91.9 | 91.9 | 91.9 | 91.9 | 89.9 | 89.9 | 89.9 |
| 2) Disintegrable granules 1[*1] | 1 | 1 | 1 | 1 | 1 | 1 | | 2 | |
| 3) Disintegrable granules 2[*2] | | | | | | | | | |
| 4) Polyethylene powder[*3] | | | | | | | | | 1 |

TABLE 2-continued

|  | Example | | | | | | Comp. Example | | |
|---|---|---|---|---|---|---|---|---|---|
| Component incorporated (%) | 13 | 14 | 15 | 16 | 17 | 18 | 1 | 2 | 3 |
| 5) dl-α-Tocopherol nicotinate |  |  |  |  |  |  | 1 |  | 1 |
| 6) Nicotinic acid amide |  |  |  |  |  |  |  |  |  |
| 7) Japanese green gentian extract |  |  |  |  |  |  | 1 |  |  |
| 8) Saint-Jone's-wort extract |  |  |  |  |  |  |  |  |  |
| 9) Ginkgo extract |  |  |  |  |  |  |  |  |  |
| 10) Arnica extract |  |  |  |  |  |  |  |  |  |
| 11) Hamamelis extract |  |  |  |  |  |  |  |  |  |
| 12) Pot marigold extract |  |  |  |  |  |  |  |  |  |
| 13) Marronnier extract | 1 |  |  |  |  |  |  |  |  |
| 14) *Isodon japonicus* Hara extract |  | 1 |  |  |  |  |  |  |  |
| 15) Scarlet sage extract |  |  | 1 |  |  |  |  |  |  |
| 16) *Glehnia littoralis* extract |  |  |  | 1 |  |  |  |  |  |
| 17) Rice germ oil |  |  |  |  | 1 |  |  |  |  |
| 18) *Tilia europaea* L extract |  |  |  |  |  | 1 |  |  |  |
| 19) Polyoxyethylene hardened castor oil | 1 | 1 | 1 | 1 | 1 | 1 | 1 | 1 | 1 |
| 20) Carboxyvinyl polymer | 0.5 | 0.5 | 0.5 | 0.5 | 0.5 | 0.5 | 0.5 | 0.5 | 0.5 |
| 21) 3% Water-soluble collagen solution | 3 | 3 | 3 | 3 | 3 | 3 | 1 | 1 | 1 |
| 22) Glycerol | 1 | 1 | 1 | 1 | 1 | 1 | 5 | 5 | 5 |
| 23) L-Arginine | 0.5 | 0.5 | 0.5 | 0.5 | 0.5 | 0.5 | 0.5 | 0.5 | 0.5 |
| 24) Perfume base | 0.01 | 0.01 | 0.01 | 0.01 | 0.01 | 0.01 | 0.01 | 0.01 | 0.01 |
| 25) Methyl p-hydroxybenzoate | 0.05 | 0.05 | 0.05 | 0.05 | 0.05 | 0.05 | 0.05 | 0.05 | 0.05 |
| Blood circulation-accelerating effect | ○ | ○ | ○ | ○ | ○ | ○ | ○ | ○ | ○ |
| Complexion-improving effect | ○ | ○ | ○ | ○ | ○ | ○ | x | ○ | ○ |
| Organoleptic evaluation (complexion improvement) | ○ | ○ | ○ | ○ | ○ | ○ | Δ | x | ○ |
| Organoleptic evaluation (feeling of irritation or physical disorder) | ○ | ○ | ○ | ○ | ○ | ○ | ○ | ○ | x |
| Overall evaluation | ○ | ○ | ○ | ○ | ○ | ○ | x | x | x |

*1:(Disintegrable granules 1) Granules prepared by using 91 wt. % of primary particles (polyethylene powder; average particle size: 5 μm) and a binder (3 wt. % of hardened rapeseed oil + 6 wt. % of hydroxypropyl cellulose) in accordance with the process described in Japanese Patent Application Laid-Open No. 271414/1994.
*2:(Disintegrable granules 2) Granules prepared by using 95 wt. % of primary particles (zinc oxide; average particle size: 3 μm) and 5 wt. % of a binder (ethyl cellulose) in accordance with the process described in Japanese Patent Application Laid-Open No. 142407/1985.
*3:(Polyethylene powder) Average particle size: 20 μm.
Examples 19 to 36 and Comparative Examples 4 to 6:
O/W type creamy complexion-improving beauty compositions were prepared by stirring and mixing components of their corresponding formulations shown in Tables 3 to 6 in accordance with a method known per se in the art. After each of the complexion-improving beauty compositions thus obtained was used to give a manual massage, the composition was washed out with hot water to evaluate it as to blood circulation-accelerating effect in the same manner as in Example 1. The results are shown in Tables 3 to 6.

TABLE 3

|  | Example | | | | | |
|---|---|---|---|---|---|---|
| Component incorporated (%) | 19 | 20 | 21 | 22 | 23 | 24 |
| 1) Purified water | 67.1 | 65.5 | 68.9 | 64.9 | 66.9 | 67.1 |
| 2) Disintegrable granules 1*1 | 1 | 0.5 | 0.5 | 2 | 0.5 | 1 |
| 3) Disintegrable granules 2*2 |  | 0.5 |  | 1 |  |  |
| 4) Polyethylene powder*3 |  |  |  |  |  |  |
| 5) dl-α-Tocopherol nicotinate | 1 | 0.5 | 0.5 | 0.5 | 0.5 |  |
| 6) Nicotinic acid amide |  |  |  |  |  | 1 |
| 7) Japanese green gentian extract |  |  |  |  |  |  |
| 8) Saint-Jone's-wort extract |  |  |  |  |  |  |
| 9) Ginkgo extract |  |  |  |  |  |  |
| 10) Arnica extract |  |  |  |  |  |  |
| 11) Hamamelis extract |  |  |  |  |  |  |
| 12) Pot marigold extract |  |  |  |  |  |  |
| 13) Marronnier extract |  |  |  | 0.5 |  |  |
| 14) *Isodon japonicus* Hara extract |  |  |  |  |  |  |
| 15) Scarlet sage extract |  |  |  |  |  |  |
| 16) *Glehnia littoralis* extract |  |  |  |  |  |  |
| 17) Rice germ oil |  |  |  |  |  |  |
| 18) *Tilia europaea* L extract |  |  |  |  |  |  |
| 19) Polyoxyethylene hardened castor oil | 0.5 | 0.5 | 0.5 | 0.5 | 0.5 | 0.5 |
| 20) Sorbitan monostearate | 1.5 | 1.5 | 0.8 | 0.8 | 0.8 | 1.5 |
| 21) Cetylphosphoric acid | 0.5 | 0.6 | 0.5 | 0.5 | 0.5 | 0.5 |
| 22) Batyl alcohol | 0.5 | 0.3 | 0.3 | 0.5 | 0.5 | 0.5 |
| 23) Cetanol | 0.9 | 1 | 0.6 | 0.9 | 0.9 | 0.9 |
| 24) Jojoba oil | 4 | 6 | 3 | 4 | 4 | 4 |
| 25) Neopentyl glycol dicaprate | 8 | 8 | 8 | 8 | 8 | 8 |
| 26) Carboxyvinyl polymer | 0.25 | 0.3 | 0.25 | 0.25 | 0.25 | 0.25 |
| 27) Chitin solution | 1 |  | 1 | 1 | 1 | 1 |
| 28) Glycerol | 10 | 14 | 12 | 12 | 12 | 10 |
| 29) 1,3-Butylene glycol | 3 |  | 2.5 | 2.5 | 2.5 | 3 |
| 30) L-Arginine | 0.5 | 0.55 | 0.5 | 0.5 | 0.5 | 0.5 |
| 31) Methyl p-hydroxy-benzoate | 0.5 | 0.3 | 0.2 | 0.2 | 0.2 | 0.3 |
| Blood circulation-accelerating effect | ○ | ○ | ○ | ○ | ○ | ○ |
| Complexion-improving effect | ○ | ○ | ○ | ○ | ○ | ○ |
| Organoleptic evaluation (complexion improvement) | ○ | ○ | Δ | ○ | ○ | ○ |
| Organoleptic evaluation (feeling of irritation or physical disorder) | ○ | ○ | ○ | ○ | ○ | ○ |
| Overall evaluation | ○ | ○ | ○ | ○ | ○ | ○ |

TABLE 4

| Component incorporated (%) | Example 25 | 26 | 27 | 28 | 29 |
|---|---|---|---|---|---|
| 1) Purified water | 65.7 | 65.7 | 65.7 | 65.7 | 65.7 |
| 2) Disintegrable granules 1[*1] | 1 | 1 | 1 | 1 | 1 |
| 3) Disintegrable granules 2[*2] | | | | | |
| 4) Polyethylene powder [*3] | | | | | |
| 5) dl-α-Tocopherol nicotinate | | | | | |
| 6) Nicotinic acid amide | | | | | |
| 7) Japanese green gentian extract | 1 | | | | |
| 8) Saint-Jone's-wort extract | | 1 | | | |
| 9) Ginkgo extract | | | 1 | | |
| 10) Arnica extract | | | | 1 | |
| 11) Hamamelis extract | | | | | 1 |
| 12) Pot marigold extract | | | | | |
| 13) *Marronnier* extract | | | | | |
| 14) *Isodon japonicus* Hara extract | | | | | |
| 15) Scarlet sage extract | | | | | |
| 16) *Glehnia littoralis* extract | | | | | |
| 17) Rice germ oil | | | | | |
| 18) *Tilia europaea L* extract | | | | | |
| 19) Polyoxyethylene hardened castor oil | 0.5 | 0.5 | 0.5 | 0.5 | 0.5 |
| 20) Sorbitan monostearate | 1.5 | 1.5 | 1.5 | 1.5 | 1.5 |
| 21) Cetylphosphoric acid | 0.5 | 0.5 | 0.5 | 0.5 | 0.5 |
| 22) Batyl alcohol | 0.5 | 0.5 | 0.5 | 0.5 | 0.5 |
| 23) Cetanol | 0.9 | 0.9 | 0.9 | 0.9 | 0.9 |
| 24) Jojoba oil | 4 | 4 | 4 | 4 | 4 |
| 25) Neopentyl glycol dicaprate | 8 | 8 | 8 | 8 | 8 |
| 26) Carboxyvinyl polymer | 0.25 | 0.25 | 0.25 | 0.25 | 0.25 |
| 27) Chitin solution | 1 | 1 | 1 | 1 | 1 |
| 28) Glycerol | 12 | 12 | 12 | 12 | 12 |
| 29) 1,3-Butylene glycol | 2.5 | 2.5 | 2.5 | 2.5 | 2.5 |
| 30) L-Arginine | 0.5 | 0.5 | 0.5 | 0.5 | 0.5 |
| 31) Methyl p-hydroxybenzoate | 0.2 | 0.2 | 0.2 | 0.2 | 0.2 |
| Blood circulation-accelerating effect | ○ | ○ | ○ | ○ | ○ |
| Complexion-improving effect | ○ | ○ | ○ | ○ | ○ |
| Organoleptic evaluation (complexion improvement) | ○ | ○ | ○ | ○ | ○ |
| Organoleptic evaluation (feeling of irritation or physical disorder) | ○ | ○ | ○ | ○ | ○ |
| Overall evaluation | ○ | ○ | ○ | ○ | ○ |

TABLE 5

| Component incorporated (%) | Example 30 | 31 | 32 | 33 | 34 | 35 |
|---|---|---|---|---|---|---|
| 1) Purified water | 65.7 | 65.7 | 65.7 | 65.7 | 65.7 | 65.7 |
| 2) Disintegrable granules 1[*1] | 1 | 1 | 1 | 1 | 1 | 1 |
| 3) Disintegrable granules 2[*2] | | | | | | |
| 4) Polyethylene powder[*3] | | | | | | |
| 5) dl-α-Tocopherol nicotinate | | | | | | |
| 6) Nicotinic acid amide | | | | | | |
| 7) Japanese green gentian extract | | | | | | |
| 8) Saint-Jone's-wort extract | | | | | | |
| 9) Ginkgo extract | | | | | | |
| 10) Arnica extract | | | | | | |
| 11) Hamamelis extract | | | | | | |
| 12) Pot marigold extract | 1 | | | | | |
| 13) Marronnier extract | | 1 | | | | |
| 14) *Isodon japonicus* Hara extract | | | 1 | | | |
| 15) Scarlet sage extract | | | | 1 | | |
| 16) *Glehnia littoralis* extract | | | | | 1 | |
| 17) Rice germ oil | | | | | | 1 |
| 18) *Tilia europaea* L extract | | | | | | |
| 19) Polyoxyethylene hardened castor oil | 0.5 | 0.5 | 0.5 | 0.5 | 0.5 | 0.5 |
| 20) Sorbitan monostearate | 1.5 | 1.5 | 1.5 | 1.5 | 1.5 | 1.5 |
| 21) Cetylphosphoric acid | 0.5 | 0.5 | 0.5 | 0.5 | 0.5 | 0.5 |
| 22) Batyl alcohol | 0.5 | 0.5 | 0.5 | 0.5 | 0.5 | 0.5 |
| 23) Cetanol | 0.9 | 0.9 | 0.9 | 0.9 | 0.9 | 0.9 |
| 24) Jojoba oil | 4 | 4 | 4 | 4 | 4 | 4 |
| 25) Neopentyl glycol dicaprate | 8 | 8 | 8 | 8 | 8 | 8 |
| 26) Carboxyvinyl polymer | 0.25 | 0.25 | 0.25 | 0.25 | 0.25 | 0.25 |
| 27) Chitin solution | 1 | 1 | 1 | 1 | 1 | 1 |
| 28) Glycerol | 12 | 12 | 12 | 12 | 12 | 12 |
| 29) 1,3-Butylene glycol | 2.5 | 2.5 | 2.5 | 2.5 | 2.5 | 2.5 |
| 30) L-Arginine | 0.5 | 0.5 | 0.5 | 0.5 | 0.5 | 0.5 |
| 31) Methyl p-hydroxybenzoate | 0.2 | 0.2 | 0.2 | 0.2 | 0.2 | 0.2 |
| Blood circulation-accelerating effect | ○ | ○ | ○ | ○ | ○ | ○ |
| Complexion-improving effect | ○ | ○ | ○ | ○ | ○ | ○ |
| Organoleptic evaluation (complexion improvement) | ○ | ○ | ○ | ○ | ○ | ○ |
| Organoleptic evaluation (feeling of irritation or physical disorder) | ○ | ○ | ○ | ○ | ○ | ○ |
| Overall evaluation | ○ | ○ | ○ | ○ | ○ | ○ |

TABLE 6

| Component incorporated (%) | Ex. 36 | Comp. Ex. 4 | 5 | 6 |
|---|---|---|---|---|
| 1) Purified water | 65.7 | 65.7 | 65.7 | 65.7 |
| 2) Disintegrable granules 1[*1] | 1 | | | |
| 3) Disintegrable granules 2[*2] | | | 2 | |
| 4) Polyethylene powder [*3] | | | | 1 |
| 5) dl-α-Tocopherol nicotinate | | 1 | | 1 |
| 6) Nicotinic acid amide | | | | |
| 7) Japanese green gentian extract | | 1 | | |
| 8) Saint-Jone's-wort extract | | | | |
| 9) Ginkgo extract | | | | |
| 10) Arnica extract | | | | |
| 11) Hamamelis extract | | | | |
| 12) Pot marigold extract | | | | |
| 13) *Marronnier* extract | | | | |
| 14) *Isodon japonicus* Hara extract | | | | |
| 15) Scarlet sage extract | | | | |
| 16) *Glehnia littoralis* extract | | | | |
| 17) Rice germ oil | | | | |
| 18) *Tilia europaea* L extract | 1 | | | |
| 19) Polyoxyethylene hardened castor oil | 0.5 | 0.5 | 0.5 | 0.5 |
| 20) Sorbitan monostearate | 1.5 | 1.5 | 1.5 | 1.5 |
| 21) Cetylphosphoric acid | 0.5 | 0.5 | 0.5 | 0.5 |
| 22) Batyl alcohol | 0.5 | 0.5 | 0.5 | 0.5 |
| 23) Cetanol | 0.9 | 0.9 | 0.9 | 0.9 |
| 24) Jojoba oil | 4 | 4 | 4 | 4 |
| 25) Neopentyl glycol dicaprate | 8 | 8 | 8 | 8 |
| 26) Carboxyvinyl polymer | 0.25 | 0.25 | 0.25 | 0.25 |
| 27) Chitin solution | 1 | 1 | 1 | 1 |
| 28) Glycerol | 12 | 12 | 12 | 12 |
| 29) 1,3-Butylene glycol | 2.5 | 2.5 | 2.5 | 2.5 |
| 30) L-Arginine | 0.5 | 0.5 | 0.5 | 0.5 |
| 31) Methyl p-hydroxybenzoate | 0.2 | 0.2 | 0.2 | 0.2 |
| Blood circulation-accelerating effect | ○ | ○ | ○ | ○ |
| Complexion-improving effect | ○ | X | X | ○ |
| Organoleptic evaluation (complexion improvement) | ○ | Δ | X | ○ |
| Organoleptic evaluation (feeling of irritation or physical disorder) | ○ | ○ | ○ | X |
| Overall evaluation | ○ | X | X | X |

Examples 37 to 56 and Comparative Examples 7 to 12

W/O type emulsified complexion-improving beauty compositions were prepared by stirring and mixing components of their corresponding formulations shown in Tables 7 to 10 in accordance with a method known per se in the art. After each of the complexion-improving beauty compositions thus obtained was used to give a manual massage, the composition was washed out with hot water to evaluate it as to blood circulation-accelerating effect etc. in the same manner as in Example 1. The results are shown in Tables 7 to 10.

TABLE 7

| Component | Example | | | | | | |
|---|---|---|---|---|---|---|---|
| incorporated (%) | 37 | 38 | 39 | 40 | 41 | 42 | 43 |
| 1) Purified water | 83.9 | 84.5 | 84.9 | 83.6 | 84.6 | 83.9 | 67.9 |
| 2) Disintegrable granules 1*1 | 1 | 0.3 | 0.5 | 1 | 0.5 | 1 | 1 |
| 3) Disintegrable granules 2*2 | | 0.3 | | 0.5 | | | |
| 4) Polyethylene powder*3 | | | | | | | |
| 5) dl-α-Tocopherol nicotinate | 0.5 | 0.5 | 0.5 | 0.3 | 0.3 | | 0.5 |
| 6) Marronnier extract | | | | | | 0.5 | |
| 7) Isotridecyl isononanoate | | | | | | | 8 |
| 8) Neopentyl glycol dicaprate | | | | | | | |
| 9) Squalane | | | | | | | 8 |
| 10) Placenta extract | | | | | | | |
| 11) Chamomile extract | | | | | | | |
| 12) Arbutin | | | | | | | |
| 13) Kojic acid | | | | | | | |
| 14) Estradiol | | | | | | | |
| 15) Royal jelly | | | | | | | |
| 16) zinc sulfocarbolate | | | | | | | |
| 17) 10-Hydroxy-undecanoic acid | | | | | | | |
| 18) Polyoxyethylene hardened castor oil | 0.5 | 0.5 | 0.5 | 0.5 | 0.5 | 0.5 | 0.5 |
| 19) Sorbitan monostearate | 1.5 | 1.5 | 1.5 | 1.5 | 1.5 | 1.5 | 1.5 |
| 20) Cetylphosphoric acid | 0.5 | 0.6 | 0.5 | 0.5 | 0.5 | 0.5 | 0.5 |
| 21) Batyl alcohol | 0.5 | 0.3 | 0.3 | 0.5 | 0.5 | 0.5 | 0.5 |
| 22) Cetanol | 0.9 | 1 | 0.6 | 0.9 | 0.9 | 0.9 | 0.9 |
| 23) Carboxyvinyl polymer | 0.15 | 0.08 | 0.15 | 0.15 | 0.15 | 0.15 | 0.15 |
| 24) Glycerol | 10 | 10 | 10 | 10 | 10 | 10 | 10 |
| 25) L-Arginine | 0.4 | 0.33 | 0.4 | 0.4 | 0.4 | 0.4 | 0.4 |
| 26) Methyl p-hydroxybenzoate | 0.1 | 0.1 | 0.1 | 0.1 | 0.1 | 0.1 | 0.1 |
| 27) Perfume base | 0.02 | 0.02 | 0.02 | 0.02 | 0.02 | 0.02 | 0.02 |
| Blood circulation-accelerating effect | ○ | ○ | ○ | ○ | ○ | ○ | ○ |
| Complexion-improving effect | ○ | ○ | ○ | ○ | ○ | ○ | ○ |
| Organoleptic evaluation (complexion improvement) | ○ | ○ | Δ | ○ | Δ | ○ | ○ |
| Organoleptic evaluation (feeling of irritation or physical disorder) | ○ | ○ | ○ | Δ | ○ | ○ | ○ |
| Overall evaluation | ○ | ○ | ○ | ○ | ○ | ○ | ○ |

TABLE 8

| Component | Example | | | | | | |
|---|---|---|---|---|---|---|---|
| incorporated (%) | 44 | 45 | 46 | 47 | 48 | 49 | 50 |
| 1) Purified water | 77.9 | 79.9 | 82.9 | 82.9 | 82.9 | 78.9 | 83.7 |
| 2) Disintegrable granules 1*1 | 1 | 1 | 1 | 1 | 1 | 1 | 1 |
| 3) Disintegrable granules 2*2 | | | | | | | |
| 4) Polyethylene powder*3 | | | | | | | |
| 5) dl-α-Tocopherol nicotinate | 0.5 | 0.5 | 0.5 | 0.5 | 0.5 | 0.5 | 0.5 |
| 6) Marronnier extract | | | | | | | |
| 7) Isotridecyl isononanoate | | | | | | | |
| 8) Neopentyl glycol dicaprate | 6 | | | | | | |
| 9) Squalane | | | | | | | |
| 10) Placenta extract | | 1 | | | | | |
| 11) Chamomile extract | | 3 | | | | | |
| 12) Arbutin | | | 1 | | | | |
| 13) Kojic acid | | | | 1 | | | |
| 14) Estradiol | | | | | 1 | | |
| 15) Royal jelly | | | | | | 5 | |
| 16) zinc sulfocarbolate | | | | | | | 0.2 |
| 17) 10-Hydroxy-undecanoic acid | | | | | | | |
| 18) Polyoxyethylene hardened castor oil | 0.5 | 0.5 | 0.5 | 0.5 | 0.5 | 0.5 | 0.5 |
| 19) Sorbitan monostearate | 1.5 | 1.5 | 1.5 | 1.5 | 1.5 | 1.5 | 1.5 |
| 20) Cetylphosphoric acid | 0.5 | 0.5 | 0.5 | 0.5 | 0.5 | 0.5 | 0.5 |
| 21) Batyl alcohol | 0.5 | 0.5 | 0.5 | 0.5 | 0.5 | 0.5 | 0.5 |
| 22) Cetanol | 0.9 | 0.9 | 0.9 | 0.9 | 0.9 | 0.9 | 0.9 |
| 23) Carboxyvinyl polymer | 0.15 | 0.15 | 0.15 | 0.15 | 0.15 | 0.15 | 0.15 |
| 24) Glycerol | 10 | 10 | 10 | 10 | 10 | 10 | 10 |
| 25) L-Arginine | 0.4 | 0.4 | 0.4 | 0.4 | 0.4 | 0.4 | 0.4 |
| 26) Methyl p-hydroxybenzoate | 0.1 | 0.1 | 0.1 | 0.1 | 0.1 | 0.1 | 0.1 |
| 27) Perfume base | 0.02 | 0.02 | 0.02 | 0.02 | 0.02 | 0.02 | 0.02 |
| Blood circulation-accelerating effect | ○ | ○ | ○ | ○ | ○ | ○ | ○ |
| Complexion-improving effect | ○ | ○ | ○ | ○ | ○ | ○ | ○ |
| Organoleptic evaluation (complexion improvement) | ○ | ○ | ○ | ○ | ○ | ○ | ○ |
| Organoleptic evaluation (feeling of irritation or physical disorder) | ○ | ○ | ○ | ○ | ○ | ○ | ○ |
| Overall evaluation | ○ | ○ | ○ | ○ | ○ | ○ | ○ |

TABLE 9

| | Comparative Example | | | | | |
|---|---|---|---|---|---|---|
| Component incorporated (%) | 51 | 52 | 53 | 54 | 55 | 56 |
| 1) Purified water | 80.9 | 71.9 | 72.9 | 71.9 | 66.9 | 68.9 |
| 2) Disintegrable granules 1*1 | 1 | 1 | 1 | 1 | 1 | 1 |
| 3) Disintegrable granules 2*2 | | | | | | |
| 4) Polyethylene powder*3 | | | | | | |
| 5) dl-α-Tocopherol nicotinate | 0.5 | 0.5 | 0.5 | 0.5 | 0.5 | 0.5 |
| 6) Marronnier extract | | | | | | |
| 7) Isotridecyl isononanoate | | 8 | 8 | 8 | | 6 |
| 8) Neopentyl glycol dicaprate | | | | | 6 | |
| 9) Squalane | | | | | 6 | 6 |
| 10) Placenta extract | | 1 | | | | |
| 11) Chamomile extract | | 3 | | 2 | | |
| 12) Arbutin | | | 1 | | | |
| 13) Kojic acid | | | | 2 | | |

TABLE 9-continued

| | Comparative Example | | | | | |
|---|---|---|---|---|---|---|
| Component incorporated (%) | 51 | 52 | 53 | 54 | 55 | 56 |
| 14) Estradiol | | | | | | 1 |
| 15) Royal jelly | | | | 4 | | |
| 16) zinc sulfocarbolate | | | | | | |
| 17) 10-Hydroxyundecanoic acid | 3 | | 3 | 2 | | |
| 18) Polyoxyethylene hardened castor oil | 0.5 | 0.5 | 0.5 | 0.5 | 0.5 | 0.5 |
| 19) Sorbitan monostearate | 1.5 | 1.5 | 1.5 | 1.5 | 1.5 | 1.5 |
| 20) Cetylphosphoric acid | 0.5 | 0.5 | 0.5 | 0.5 | 0.5 | 0.5 |
| 21) Batyl alcohol | 0.5 | 0.5 | 0.5 | 0.5 | 0.5 | 0.5 |
| 22) Cetanol | 0.9 | 0.9 | 0.9 | 0.9 | 0.9 | 0.9 |
| 23) Carboxyvinyl polymer | 0.15 | 0.15 | 0.15 | 0.15 | 0.15 | 0.15 |
| 24) Glycerol | 10 | 10 | 10 | 10 | 10 | 10 |
| 25) L-Arginine | 0.4 | 0.4 | 0.4 | 0.4 | 0.4 | 0.4 |
| 26) Methyl p-hydroxybenzoate | 0.1 | 0.1 | 0.1 | 0.1 | 0.1 | 0.1 |
| 27) Perfume base | 0.02 | 0.02 | 0.02 | 0.02 | 0.02 | 0.02 |
| Blood circulation-accelerating effect | ○ | ○ | ○ | ○ | ○ | ○ |
| Complexion-improving effect | ○ | ○ | ○ | ○ | ○ | ○ |
| Organoleptic evaluation (complexion improvement) | ○ | ○ | ○ | ○ | ○ | ○ |
| Organoleptic evaluation (feeling of irritation or physical disorder) | ○ | ○ | ○ | ○ | ○ | x |
| Overall evaluation | ○ | ○ | ○ | ○ | ○ | ○ |

TABLE 10

| | Comparative Example | | | | | |
|---|---|---|---|---|---|---|
| Component incorporated (%) | 7 | 8 | 9 | 10 | 11 | 12 |
| 1) Purified water | 84.4 | 84.4 | 70.4 | 69.4 | 69.4 | 67.4 |
| 2) Disintegrable granules 1*1 | 1 | | | 1 | | |
| 3) Disintegrable granules 2*2 | | | | | | |
| 4) Polyethylene powder*3 | | | | | | 2 |
| 5) dl-α-Tocopherol nicotinate | | 1 | | | 1 | 1 |
| 6) Marronnier extract | | | | | | |
| 7) Isotridecyl isononanoate | | | 6 | 6 | 6 | 6 |
| 8) Neopentyl glycol dicaprate | | | | | | |
| 9) Squalane | | | 6 | 6 | 6 | 6 |
| 10) Placenta extract | | | | | | |
| 11) Chamomile extract | | | | | | |
| 12) Arbutin | | | | | | |
| 13) Kojic acid | | | 2 | 2 | 2 | 2 |
| 14) Estradiol | | | 1 | 1 | 1 | 1 |
| 15) Royal jelly | | | | | | |
| 16) zinc sulfocarbolate | | | | | | |
| 17) 10-Hydroxyundecanoic acid | | | | | | |
| 18) Polyoxyethylene hardened castor oil | 0.5 | 0.5 | 0.5 | 0.5 | 0.5 | 0.5 |
| 19) Sorbitan monostearate | 1.5 | 1.5 | 1.5 | 1.5 | 1.5 | 1.5 |
| 20) Cetylphosphoric acid | 0.5 | 0.5 | 0.5 | 0.5 | 0.5 | 0.5 |
| 21) Batyl alcohol | 0.5 | 0.5 | 0.5 | 0.5 | 0.5 | 0.5 |
| 22) Cetanol | 0.9 | 0.9 | 0.9 | 0.9 | 0.9 | 0.9 |
| 23) Carboxyvinyl polymer | 0.15 | 0.15 | 0.15 | 0.15 | 0.15 | 0.15 |
| 24) Glycerol | 10 | 10 | 10 | 10 | 10 | 10 |
| 25) L-Arginine | 0.4 | 0.4 | 0.4 | 0.4 | 0.4 | 0.4 |
| 26) Methyl p-hydroxybenzoate | 0.1 | 0.1 | 0.1 | 0.1 | 0.1 | 0.1 |
| 27) Perfume base | 0.02 | 0.02 | 0.02 | 0.02 | 0.02 | 0.02 |
| Blood circulation-accelerating effect | x | ○ | x | x | ○ | ○ |
| Complexion-improving effect | x | x | x | ○ | x | ○ |
| Organoleptic evaluation (complexion improvement) | x | Δ | x | Δ | ○ | ○ |
| Organoleptic evaluation (feeling of irritation or physical disorder) | ○ | ○ | ○ | ○ | ○ | x |
| Overall evaluation | x | x | x | x | x | x |

Examples 57 to 76 and Comparative Examples 13 to 18

O/W type creamy complexion-improving beauty compositions were prepared by stirring and mixing components of their corresponding formulations shown in Tables 11 to 14 in accordance with a method known per se in the art. After each of the complexion-improving beauty compositions thus obtained was used to give a manual massage, the composition was washed out with hot water to evaluate it as to blood circulation-accelerating effect etc. in the same manner as in Example 1. The results are shown in Tables 11 to 14.

TABLE 11

| Component incorporated (%) | Example | | | | | | |
|---|---|---|---|---|---|---|---|
| | 57 | 58 | 59 | 60 | 61 | 62 | 63 |
| 1) Purified water | 46.7 | 47.1 | 47.2 | 46.4 | 47.4 | 46.7 | 30.7 |
| 2) Disintegrable granules 1*1 | 1 | 0.3 | 0.5 | 1 | 0.5 | 1 | 1 |
| 3) Disintegrable granules 2*2 | | 0.3 | | 0.5 | | | |
| 4) Polyethylene powder*3 | | | | | | | |
| 5) dl-α-Tocopherol nicotinate | 0.5 | 0.5 | 0.5 | 0.3 | 0.3 | | 0.5 |
| 6) Marronnier extract | | | | | | 0.5 | |
| 7) Isotridecyl isononanoate | | | | | | | 8 |
| 8) Neopentyl glycol dicaprate | | | | | | | |
| 9) Squalane | | | | | | | 8 |
| 10) Placenta extract | | | | | | | |
| 11) Chamomile extract | | | | | | | |
| 12) Arbutin | | | | | | | |
| 13) Kojic acid | | | | | | | |
| 14) Estradiol | | | | | | | |
| 15) Royal jelly | | | | | | | |
| 16) zinc sulfocarbolate | | | | | | | |
| 17) 10-Hydroxyundecanoic acid | | | | | | | |
| 18) Isostearyl glyceryl ether | 1 | 1 | 1 | 1 | 1 | 1 | 1 |
| 19) POE-Modified polysiloxane polymer | 4 | 4 | 4 | 4 | 4 | 4 | 4 |
| 20) Sphingo lipid E | 8 | 8 | 8 | 8 | 8 | 8 | 8 |
| 21) Methyl polysiloxane | 20 | 20 | 20 | 20 | 20 | 20 | 20 |
| 22) Monocholesteryl alkenylsuccinate | 0.3 | 0.3 | 0.3 | 0.3 | 0.3 | 0.3 | 0.3 |
| 23) Magnesium sulfate | 1 | 1 | 1 | 1 | 1 | 1 | 1 |
| 24) Glycerol | 15 | 15 | 15 | 15 | 15 | 15 | 15 |
| 25) Sodium citrate | 1.5 | 1.5 | 1.5 | 1.5 | 1.5 | 1.5 | 1.5 |
| 26) Citric acid | 0.5 | 0.5 | 0.5 | 0.5 | 0.5 | 0.5 | 0.5 |
| 27) Dextrin palmitate | 0.5 | 0.5 | 0.5 | 0.5 | 0.5 | 0.5 | 0.5 |
| Blood circulation-accelerating effect | ○ | ○ | ○ | ○ | ○ | ○ | ○ |
| Complexion-improving effect | ○ | ○ | ○ | ○ | ○ | ○ | ○ |
| Organoleptic evaluation (complexion improvement) | ○ | ○ | ○ | ○ | ○ | ○ | ○ |
| Organoleptic | ○ | ○ | ○ | ○ | ○ | ○ | ○ |

TABLE 11-continued

| Component incorporated (%) | Example | | | | | | |
|---|---|---|---|---|---|---|---|
| | 57 | 58 | 59 | 60 | 61 | 62 | 63 |
| evaluation (feeling of irritation or physical disorder) | | | | | | | |
| Overall evaluation | ○ | ○ | ○ | ○ | ○ | ○ | ○ |

TABLE 12

| Component incorporated (%) | Example | | | | | | |
|---|---|---|---|---|---|---|---|
| | 64 | 65 | 66 | 67 | 68 | 69 | 70 |
| 1) Purified water | 40.7 | 42.7 | 45.7 | 45.7 | 45.7 | 41.7 | 46.5 |
| 2) Disintegrable granules 1*1 | 1 | 1 | 1 | 1 | 1 | 1 | 1 |
| 3) Disintegrable granules 2*2 | | | | | | | |
| 4) Polyethylene powder*3 | | | | | | | |
| 5) dl-α-Tocopherol nicotinate | 0.5 | 0.5 | 0.5 | 0.5 | 0.5 | 0.5 | 0.5 |
| 6) Marronnier extract | | | | | | | |
| 7) Isotridecyl isononanoate | | | | | | | |
| 8) Neopentyl glycol dicaprate | 6 | | | | | | |
| 9) Squalane | | | | | | | |
| 10) Placenta extract | | 1 | | | | | |
| 11) Chamomile extract | | 3 | | | | | |
| 12) Arbutin | | | 1 | | | | |
| 13) Kojic acid | | | | 1 | | | |
| 14) Estradiol | | | | | 1 | | |
| 15) Royal jelly | | | | | | 5 | |
| 16) zinc sulfocarbolate | | | | | | | 0.2 |
| 17) 10-Hydroxy-undecanoic acid | | | | | | | |
| 18) Isostearyl glyceryl ether | 1 | 1 | 1 | 1 | 1 | 1 | 1 |
| 19) POE-Modified polysiloxane polymer | 4 | 4 | 4 | 4 | 4 | 4 | 4 |
| 20) Sphingo lipid E | 8 | 8 | 8 | 8 | 8 | 8 | 8 |
| 21) Methyl polysiloxane | 20 | 20 | 20 | 20 | 20 | 20 | 20 |
| 22) Monocholesteryl alkenylsuccinate | 0.3 | 0.3 | 0.3 | 0.3 | 0.3 | 0.3 | 0.3 |
| 23) Magnesium sulfate | 1 | 1 | 1 | 1 | 1 | 1 | 1 |
| 24) Glycerol | 15 | 15 | 15 | 15 | 15 | 15 | 15 |
| 25) Sodium citrate | 1.5 | 1.5 | 1.5 | 1.5 | 1.5 | 1.5 | 1.5 |
| 26) Citric acid | 0.5 | 0.5 | 0.5 | 0.5 | 0.5 | 0.5 | 0.5 |
| 27) Dextrin palmitate | 0.5 | 0.5 | 0.5 | 0.5 | 0.5 | 0.5 | 0.5 |
| Blood circulation-accelerating effect | ○ | ○ | ○ | ○ | ○ | ○ | ○ |
| Complexion-improving effect | ○ | ○ | ○ | ○ | ○ | ○ | ○ |
| Organoleptic evaluation (complexion improvement) | ○ | ○ | ○ | ○ | ○ | ○ | ○ |
| Organoleptic evaluation (feeling of irritation or physical disorder) | ○ | ○ | ○ | ○ | ○ | ○ | ○ |
| Overall evaluation | ○ | ○ | ○ | ○ | ○ | ○ | ○ |

TABLE 13

| Component incorporated (%) | Example | | | | | |
|---|---|---|---|---|---|---|
| | 71 | 72 | 73 | 74 | 75 | 76 |
| 1) Purified water | 43.7 | 34.7 | 35.7 | 34.7 | 29.7 | 31.7 |
| 2) Disintegrable granules 1*1 | 1 | 1 | 1 | 1 | 1 | 1 |
| 3) Disintegrable granules 2*2 | | | | | | |
| 4) Polyethylene powder*3 | | | | | | |
| 5) dl-α-Tocopherol nicotinate | 0.5 | 0.5 | 0.5 | 0.5 | 0.5 | 0.5 |
| 6) Marronnier extract | | | | | | |
| 7) Isotridecyl isononanoate | | 8 | 8 | 8 | | 6 |
| 8) Neopentyl glycol dicaprate | | | | | 6 | |
| 9) Squalane | | | | | 6 | 6 |
| 10) Placenta extract | | 1 | | | | |
| 11) Chamomile extract | | 3 | | 2 | | |
| 12) Arbutin | | | | | 1 | |
| 13) Kojic acid | | | | | | 2 |
| 14) Estradiol | | | | | | 1 |
| 15) Royal jelly | | | | | 4 | |
| 16) zinc sulfocarbolate | | | | | | |
| 17) 10-Hydroxyundecanoic acid | 3 | | 3 | 2 | | |
| 18) Isostearyl glyceryl ether | 1 | 1 | 1 | 1 | 1 | 1 |
| 19) POE-Modified polysiloxane polymer | 4 | 4 | 4 | 4 | 4 | 4 |
| 20) Sphingo lipid E | 8 | 8 | 8 | 8 | 8 | 8 |
| 21) Methyl polysiloxane | 20 | 20 | 20 | 20 | 20 | 20 |
| 22) Monocholesteryl alkenylsuccinate | 0.3 | 0.3 | 0.3 | 0.3 | 0.3 | 0.3 |
| 23) Magnesium sulfate | 1 | 1 | 1 | 1 | 1 | 1 |
| 24) Glycerol | 15 | 15 | 15 | 15 | 15 | 15 |
| 25) Sodium citrate | 1.5 | 1.5 | 1.5 | 1.5 | 1.5 | 1.5 |
| 26) Citric acid | 0.5 | 0.5 | 0.5 | 0.5 | 0.5 | 0.5 |
| 27) Dextrin palmitate | 0.5 | 0.5 | 0.5 | 0.5 | 0.5 | 0.5 |
| Blood circulation-accelerating effect | ○ | ○ | ○ | ○ | ○ | ○ |
| Complexion-improving effect | ○ | ○ | ○ | ○ | ○ | ○ |
| Organoleptic evaluation (complexion improvement) | ○ | ○ | ○ | ○ | ○ | ○ |
| Organoleptic evaluation (feeling of irritation or physical disorder) | ○ | ○ | ○ | ○ | ○ | ○ |
| Overall evaluation | ○ | ○ | ○ | ○ | ○ | ○ |

TABLE 14

| Component incorporated (%) | Comparative Example | | | | | |
|---|---|---|---|---|---|---|
| | 13 | 14 | 15 | 16 | 17 | 18 |
| 1) Purified water | 47.2 | 47.2 | 33.2 | 32.2 | 32.2 | 30.2 |
| 2) Disintegrable granules 1*1 | 1 | | | 1 | | |
| 3) Disintegrable granules 2*2 | | | | | | |
| 4) Polyethylene powder*3 | | | | | | 2 |
| 5) dl-α-Tocopherol nicotinate | | 1 | | | 1 | 1 |
| 6) Marronnier extract | | | | | | |
| 7) Isotridecyl isononanoate | | | 6 | 6 | 6 | 6 |
| 8) Neopentyl glycol dicaprate | | | | | | |
| 9) Squalane | | | 6 | 6 | 6 | 6 |
| 10) Placenta extract | | | | | | |
| 11) Chamomile extract | | | | | | |
| 12) Arbutin | | | | | | |
| 13) Kojic acid | | | 2 | 2 | 2 | 2 |
| 14) Estradiol | | | 1 | 1 | 1 | 1 |
| 15) Royal jelly | | | | | | |
| 16) zinc sulfocarbolate | | | | | | |
| 17) 10-Hydroxyundecanoic acid | | | | | | |
| 18) Isostearyl glyceryl ether | 1 | 1 | 1 | 1 | 1 | 1 |
| 19) POE-Modified polysiloxane polymer | 4 | 4 | 4 | 4 | 4 | 4 |
| 20) Sphingo lipid E | 8 | 8 | 8 | 8 | 8 | 8 |

TABLE 14-continued

| | Comparative Example | | | | | |
|---|---|---|---|---|---|---|
| Component incorporated (%) | 13 | 14 | 15 | 16 | 17 | 18 |
| 21) Methyl polysiloxane | 20 | 20 | 20 | 20 | 20 | 20 |
| 22) Monocholesteryl alkenylsuccinate | 0.3 | 0.3 | 0.3 | 0.3 | 0.3 | 0.3 |
| 23) Magnesium sulfate | 1 | 1 | 1 | 1 | 1 | 1 |
| 24) Glycerol | 15 | 15 | 15 | 15 | 15 | 15 |
| 25) Sodium citrate | 1.5 | 1.5 | 1.5 | 1.5 | 1.5 | 1.5 |
| 26) Citric acid | 0.5 | 0.5 | 0.5 | 0.5 | 0.5 | 0.5 |
| 27) Dextrin palmitate | 0.5 | 0.5 | 0.5 | 0.5 | 0.5 | 0.5 |
| Blood circulation-accelerating effect | x | ○ | x | x | ○ | ○ |
| Complexion-improving effect | x | x | x | ○ | x | ○ |
| Organoleptic evaluation (complexion improvement) | x | Δ | x | Δ | ○ | ○ |
| Organoleptic evaluation (feeling of irritation or physical disorder) | ○ | ○ | ○ | ○ | ○ | x |
| Overall evaluation | x | x | x | x | x | x |

As apparent from the results shown in Tables 1 to 14, the invention products are all excellent in blood circulation-accelerating effect and complexion-improving effect and do not irritate the skin and eyes, thus being highly safe.

Incidentally, the disclosure of Japanese Patent Application No. 78682/1996 is incorporated herein by reference.

The complexion-improving beauty compositions according to the present invention comprise disintegrable granules, which are easily disintegrated on the skin, and a blood circulation accelerator, i.e., a component for positively improving peripheral circulation, whereby the respective physical blood circulation-accelerating effect and chemical blood circulation-accelerating effect are synergistically enhanced to improve a complexion. In addition, the disintegrable granules penetrate into pores of various sizes in the skin surface while they are being disintegrated, so that physical irritation corresponding to the size of the granules at this time is applied to the skin to facilitate the smooth penetration of the blood circulation accelerator. Therefore, the beauty compositions are excellent in the effect of preventing and improving the irregularity, dinginess and lusterlessness of a complexion, which are caused by the irregularity of blood circulation. Furthermore, there is no need to incorporate the blood circulation accelerator in a large amount in virtue of the above synergistic effect, and the use of the disintegrable granules prevents the skin and eyes from being irritated, so that the beauty compositions are highly safe.

What is claimed is:

1. A complexion improving beauty composition comprising 0.1 to 0.5 wt. % disintegrable granules and 0.001 to 5 wt. % of a blood circulation accelerator.

2. The complexion-improving beauty composition according to claim 1, wherein the disintegrable granules are composed of a water-insoluble primary particles and a binder.

3. The complexion-improving beauty composition according to claim 2, wherein the particle size of the disintegrable granules is 100 to 1,000 μm, and at least 80 wt. % of the primary particles have a particle size of at most 10 μm.

4. The complexion-improving beauty composition according to any one of claims 1–3, wherein the blood circulation accelerator is selected from tocopherol nicotinate, nicotinic acid amide, Japanese green gentian extract, Saint-Jone's-wort extract, ginkgo extract, arnica extract, hamamelis extract, pot marigold extract, *marronnier* extract, *Isodon japonicus* Hara extract, scarlet sage extract, *Glehnia littoralis* extract, rice germ oil and *Tilia europaea* L extract.

5. The complexion-improving beauty composition according to any one of claims 1–3, which further comprises an oily substance having a refractive index of at least 1.444 or an SP value of at least 16.5.

6. The complexion-improving beauty composition according to claim 5, wherein the oily substance is selected from isotridecyl isononanoate, neopentyl glycol dicaprate, 1-isostearoyl-3-myristoylglycerol, glyceryl tri-2-ethylhexanoate, squalane, 1,3-myristoyl-glycerol, diglyceryl monoisostearate, diglyceryl diisostearate, diglyceryl triisostearate and octyldodecyl lactate.

7. The complexion-improving beauty composition according to any one of claims 1–3, which further comprises a whitening agent.

8. The complexion-improving beauty composition according to claim 7, wherein the whitening agent is selected from L-ascorbic acid, arbutin, kojic acid, placenta extracts, chamomile extract, tea plant extract, puerariae root extract and licorice extract.

9. The complexion-improving beauty composition according to any one of claims 1–3, which further comprises a sebum secretion inhibitor.

10. The complexion-improving beauty composition according to claim 9, wherein the sebum secretion inhibitor is selected from estradiol, zinc sulfocarbolate, zinc oxide, royal jelly, 10-hydroxy-undecanoic acid and 12-hydroxystearic acid.

11. A method of improving a complexion, which comprises applying the composition according to any one of claims 1–3, to the skin and then massaging or rubbing the skin applied.

12. The method according to claim 11, wherein the massaging or rubbing is continued until the disintegrable granules are disintegrated.

\* \* \* \* \*